United States Patent [19]

Asadoorian

[11] Patent Number: Plant 6,348

[45] Date of Patent: Oct. 25, 1988

[54] GRAPEVINE MICALA

[76] Inventor: Alan J. Asadoorian, 1141 W. Scott, Fresno, Calif. 93711

[21] Appl. No.: 942,090

[22] Filed: Dec. 15, 1986

[51] Int. Cl.[4] ..... A01H 5/03
[52] U.S. Cl. ..... Plt./47
[58] Field of Search ..... Plt./47

*Primary Examiner*—Robert E. Bagwill

*Attorney, Agent, or Firm*—Worrel & Worrel

[57] ABSTRACT

A new and distinct grapevine denominated varietally as Micala generally resembling the Ribier Grapevine (unpatented) but characterized as to novelty by producing grapes which are ready for harvest approximately August 5 to August 15 at Fowler, Calif., and furthermore by producing berries which are substantially seedless and which have a dark substantially black color.

1 Drawing Sheet

BACKGROUND OF THE NEW VARIETY

The present invention relates to a new and distinct variety of grapevine denominated varietally as Micala, and more particularly to a grapevine which is somewhat similar in physical characteristics to the Black Beauty Seedless Grapevine, (unpatented) and to the known Ribier Grapevine (unpatented), from which it was derived as a progeny following the successful cross-pollinization of the two designated unpatented varieties, but from which it is distinguished as to novelty in its production of a black seedless berry which is mature for harvesting approximately four to six weeks later than the Black Beauty Seedless Grapevine and which is otherwise distinguishable from the Ribier grapevine in producing berries which are significantly larger in size and shape.

In a continuing effort to upgrade the quality of his grapes, the applicant has from time to time cross-pollinated grapevines having desirable characteristics in the hope of developing a new and distinct variety of grapevine which he could later introduce to the market. In these labors to produce a new variety of grapevine, the applicant has routinely cross-pollinated parent grapevines having known desirable traits, grown the resulting progeny to maturity, and thereafter carefully studied the progeny's characteristics to determine whether or not a new variety of grape has been produced. The instant variety of grapevine resulted from this procedure.

As noted above, the grapevine of the new variety is noteworthy in its production of its berries from four to six weeks later than the Black Beauty Grapevine, one of the parents of the instant variety; and for producing an almost seedless black berry which varies significantly in size and shape from the Ribier Grapevine, the Ribier Grapevine being known as the producer of a black seeded table grape that matures approximately in the same season as the new variety of grapevine described herein.

ORIGIN AND ASEXUAL REPRODUCTION OF THE NEW VARIETY

The present variety of grapevine is the progeny produced from the successful cross-pollination of a female Ribier Grapevine (unpatented), and a male Black Beauty Seedless grapevine (unpatented) performed at a ranch located at 8601 Adams Ave. in Fowler, County of Fresno, State of California. This successful cross-pollination which was performed in the Spring of 1979 produced progeny which were observed for several years prior to a full recognition of their desirable characteristics. The applicant asexually reproduced the instant grapevine by taking cuttings from the original parent vine and growing them to maturity as scions at the applicant's ranch which is located on the southwest corner of American and Minnewawa Aves. in Fresno, Calif. The pomological characteristics of the grapevines resulting from this first asexual reproduction were observed by the applicant and it was thereafter determined that they were identical to that of the original parent. The first evaluation of the instant grapevine was conducted in 1984 and subsequent evaluations were made in 1985 and 1986.

BRIEF DESCRIPTION OF THE DRAWING

The accompanying drawing is a color photograph of a bunch of grapes of the subject variety sufficiently mature for harvesting and shipment, several leaves showing their dorsal and ventral coloration and a typical section of the vine, all of the instant variety.

DETAILED DESCRIPTION

Referring more specifically to the pomological details of this new and distinct variety of grapevine, the following has been observed under the ecological conditions prevailing at the applicant's ranch which is located near Fowler, Calif. with due regard for cultural practices.

VINE

Size: Generally—large.

Form: Upright, dense and tender; the subject variety was described as it was growing on a gable trellis system. It is estimated that a gable trellis might influence, to some slight degree, the growth and productivity of the instant grapevine.

Vigor: Vigorous.

Productivity: Productive; the average shoot normally produces two and sometimes three clusters of grapes. It is estimated that a mature vine of this variety which is growing under typical central San Joaquin Valley growing conditions will produce one (1) to one and one-half (1.5) lugs; (23 lbs. per lug) of grapes per vine.

Trunk:

*Size.*—Generally — large, the trunk is high as compared with other varieties.

*Width.*—Medium.

*Bark.*—Texture — loose and shreddy; the bark texture of this variety is typical for a viniferous grape.

Canes:

*Length.*—Long; approximately 150 to 300 cm.

*Numbers.*—Average.

*Width.*—Medium; approximately 8 to 20 mm.

*Color.*—Brown.

*Form.*—Straight.

*Nodes.*—Present; generally enlarged.

*Internodes.*—Size — medium; approximately 6.0 to 13.5 cm., average size is approximately 9.7 cm.

Tendrils: Generally—intermittent.

*Thickness.*—Slender.

*Length.*—Long.

*Form.*—Trifurcated, although occasionally a few bifurcated may be found.

*Texture.*—Smooth.

*Numbers.*—Abundant.

Flowers: Generally — fertile, with upright stamens.

*Date of bloom.*—Average, as compared with other varieties; the earliest date of bloom was noted to be May 4, and full bloom was achieved approximately May 10; this date of bloom is approximately 3 to 4 days after the bloom date of the Thompson Seedless variety in the San Joaquin Valley of Central California.

LEAVES

Size: Generally — average, as compared to other varieties.

*Length.*—Variable; approximately 8.4 through 12.5 cm.

*Width.*—Variable; approximately 10.4 through 11.3 cm.

*Thickness.*—Thin; approximately 0.37 through 0.63 cm.

*Surface area.*—Approximately 115 through 120 $cm^2$.

*Color.*—Dorsal surface — yew green, (Plate 24-L-7), page 71. Ventral surfce — cedar green, (Plate 23-L-6), page 69.

*Texture.*—Dorsal surface — smooth.

*Pubescence.*—Generaly — glabrous.

*Lobes.*—Numbers — variable, 3 to 5; however, most mature leaves have 5 lobes. Terminal lobes — position — obtuse.

*Petiolar sinus.*—Generally — deep; closed or alternatively overlapping in appearance.

*Basal sinus.*—Size — average, occasionally shallow. Width — medium.

*Lateral sinus.*—Length — deep.

*Width.*—Variable, average, occasionally wide.

*Margin.*—Form — dentate with slightly convex sides.

*Teeth.*—Depth — average. Width — average — medium.

FRUIT

Maturity when described: Ripe for harvesting; ripening date is affected by the climatic conditions in the San Joaquin Valley of Central California. In 1986, the instant variety was mature for harvesting approximately August 3 through August 5. However, the anticipated ripening date in an average season is estimated to be approximately August 5 through August 15. The date of ripening is average as compared to other grape varieties having similar characteristics.

*Storage quality.*—The present variety has been kept in cold storage up to and including three weeks with no deleterious effects noted.

*Shipping quality.*—Unknown.

Cluster:

*Size.*—Generally — medium to large.

*Length.*—Variable; approximately 22 through 27 cm.

*Weight.*—Variable; approximately 659 through 879 grams; it should be understood, however, that tipped clusters, and clusters receiving applications of gibberellic acid may exhibit sizes and weights which vary from the ranges expressed herein.

*Form.*—Medium; tapering; regular; and mixed, displaying both single and double shouldered forms.

*Density.*—Medium; well filled.

*Peduncle.*—Length — medium; approximately 3.4 through 6.8 cm. Thickness — generally — average; the thickness may be influenced by the application of gibberellic acid.

*Pedicle.*—Length — short; approximately 8.94 through 9.62 mm. Thickness — slender, approximately 0.98 through 1.14 mm. Warts — present; numbers — numerous.

*Brush.*—Length — short. Color — a very light pink.

Berry:

*Shells.*—Mediumly adherent.

Size.—Generally — average.

*Shape.*—Uniform, oval.

*Color.*—A very dark red with a bluish hue; the variety most closely resembles the color of the Ribier table grape (unpatented), with which it is most closely related, (84 L-9 or 84 L-10).

*Bloom.*—A thin bloom is present.

*Length.*—Approximately 21.27 through 22.13 mm.

*Diameter.*—Approximately 16.78 through 18.32 mm.

*Berry weight.*—Approximately 3.74 through 3.86 grams.

*Percent soluble solids.*—Approximately 18% at maturity.

*Acidity.*—(*as expressed in grams of acid per* 100 *cc of juice*).—Approximately 0.81%.

*Sugar/acid ratio.*—Variable; approximately 22:1 through 25:1; the new variety slightly exceeds the minimum sugar or sugar/acid ratio requirements.

Skin:

*Thickness.*—Thin.

*Texture.*—Tender.

*Adherence to the pulp.*—Adheres; this characteristic is typical of viniferous grapes.

Flesh

*Color.*—White and translucent.

*Texture.*—Soft; tender; juicy and sweet.

*Quality.*—Good.

*Seeds.*—Only seed traces were detected; an average number of 1.5 seed traces per berry were found.

Use: Fresh market, and dessert.

Although the new variety of grapevine possesses the described characteristics as the result of the growing conditions prevailing in the San Joaquin Valley of Central California, it is to be understood that variations of the usual magnitude and characteristics incident to growing conditions, fertilization, pruning and pest control are to be expected.

Having thus described and illustrated my new variety of grapevine, I claim:

1. A new and distinct variety of grapevine to be denominated varietally as Micala substantially as illustrated and described and which is characterized principally as to novelty by its production of a substantially black seedless berry which is mature for harvesting approximately August 5 to August 15 in Fowler, Calif., said grapes maturing in approximately the same season as the fruit produced by the Ribier Grapevine (unpatented) with which it most closely resembles, but from which it is distinguished by producing berries which are substantially seedless and which are significantly different in both size and shape from the Ribier Grapevine.

* * * * *

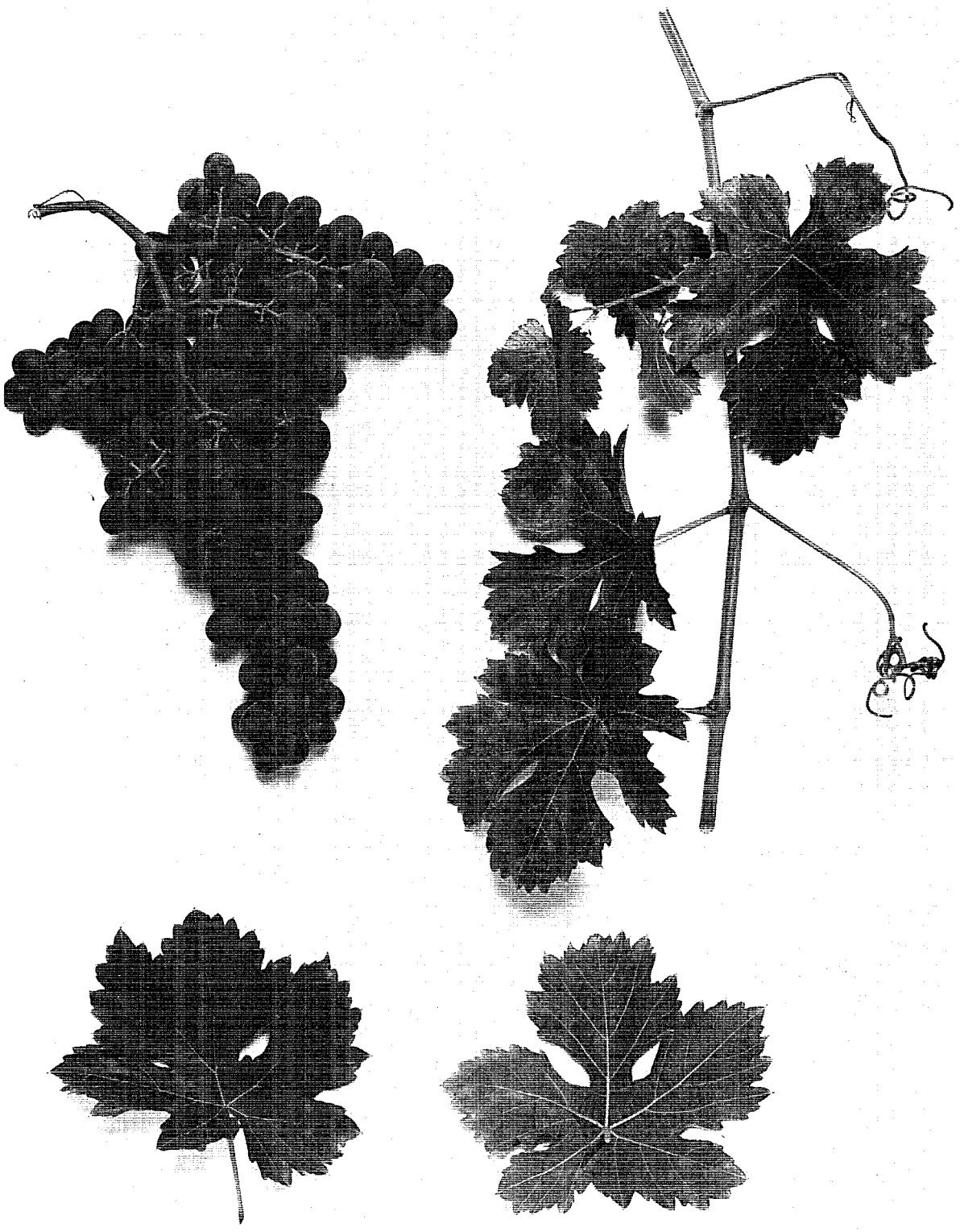

UNITED STATES PATENT AND TRADEMARK OFFICE

CERTIFICATE OF CORRECTION

PATENT NO. : PP 6,348

DATED : October 25, 1988

INVENTOR(S) : Alan J. Asadoorian

It is certified that error appears in the above-identified patent and that said Letters Patent is hereby corrected as shown below:

In the Specification:

Col. 2, line 31, after "cultural practices" insert the following:

The color code identifications are by reference to the Maerz and Paul Dictionary of Color, Second Edition, 1950. Common descriptive color names are also employed occasionally.

Signed and Sealed this

Seventh Day of March, 1989

*Attest:*

DONALD J. QUIGG

*Attesting Officer*

*Commissioner of Patents and Trademarks*